United States Patent [19]
Kieffer

[11] Patent Number: 6,048,327
[45] Date of Patent: Apr. 11, 2000

[54] ATHLETIC SUPPORTER WITH GEL MATERIAL

[76] Inventor: Doreen M. Kieffer, 22 Virginia Ridge Rd., Sudbury, Mass. 01776

[21] Appl. No.: 08/802,755

[22] Filed: Feb. 20, 1997

[51] Int. Cl.[7] .................................................. A61F 5/40
[52] U.S. Cl. ............................................. 602/70; 607/108
[58] Field of Search ................................. 602/67, 70, 73; 607/96, 108, 114; 2/455; 450/403, 267, 228, 405, 38; 128/95.1, 96.1, 98.1; 623/7; 604/352, 353, 395

[56] References Cited

U.S. PATENT DOCUMENTS

| Re. 34,573 | 4/1994 | Calvert | 2/228 |
|---|---|---|---|
| 1,830,572 | 11/1931 | Taylor . | |
| 3,787,892 | 1/1974 | Quinn | 602/67 |
| 3,788,314 | 1/1974 | Noreen | 602/67 |
| 4,043,329 | 8/1977 | DiMatteo . | |
| 4,125,117 | 11/1978 | Lee | 423/7 |
| 4,257,414 | 3/1981 | Gamm et al. | 602/67 |
| 5,037,436 | 8/1991 | Heaston | 623/7 |
| 5,103,505 | 4/1992 | Llorens . | |
| 5,167,655 | 12/1992 | McCoy | 604/395 |
| 5,243,974 | 9/1993 | Allen . | |
| 5,354,337 | 10/1994 | Hoy | 623/7 |
| 5,405,312 | 4/1995 | Jacobs | 602/5 |

*Primary Examiner*—Jerome Donnelly
*Attorney, Agent, or Firm*—Maura K. Moran

[57] ABSTRACT

A cushioning pad, sized to be disposed about the inguinal area of a human male and to be worn for the support and protection of said area, contains a gel material to protect against both localized blows and chafing. The pad fits into a protective garment having a securing means for securing it about the inguinal area. In one embodiment, the pad further comprises an inner layer of gel material, an outer layer of gel material, and a layer of shaping material disposed therebetween. The layer of shaping material may be sized to be shorter and narrower than the inner layer and outer layer of gel material so that the layer of shaping material is completely interior to the cushioning pad, and no sharp or blunt plastic edges can come into contact with the body of the athlete. In a further aspect of the invention, a protective garment to be worn for the support and protection of the inguinal area comprises a waist band, a pouch disposed about the inguinal area when the garment is worn, and, disposed within the pouch, a cushioning pad containing a gel material. Methods for forming a cushioning pad are also disclosed. One method comprises pouring into a mold an inner layer of gel material; fitting, above the inner layer, a layer of shaping material having an outer edge; and pouring an outer layer of gel material. Another method discloses pouring into a mold the inner layer of gel material. When the gel material is partially set, a layer of shaping material is fitted and pressed into the inner layer so that the gel material oozes up and over the outer edge of the layer of shaping material to form an outer layer of gel material. In yet another embodiment, the pad is formed by forming a first and second sheets of gel; and attaching the layer of shaping material therebetween.

16 Claims, 2 Drawing Sheets

ATHLETIC SUPPORTER WITH GEL MATERIAL

BACKGROUND OF THE INVENTION

This invention relates generally to support garments and particularly to an athletic garment for the support and protection of the inguinal area of a human male.

Athletic supporters are in common use to reduce the probability of injury to the scrotum or groin, or inguinal area. Typically, such supporters comprise a cup garment 10, such as one shown in FIG. 1, comprising an elastic waist band 12 and a pouch 14 sewn to the front of the waist band 12 and depending downward from the waist band 12. A pair of leg straps 16 is sewn to the bottom of the pouch 14 and to opposite sides of the waist band 12 at positions removed from the top of the pouch 14. The pouch 14 has a top-opening pocket 18, disposed to open to one of either the front or rear of the pouch 18, that receives a rigid shield or "cup" 20. The cup 20 has perforations 22, to give the cup 20 lightness, and foam padding 24 stretched around its rim.

In use, the cup 20, held in position over the inguinal area by the supporter 10, protects the inguinal areas from localized blows. However, the cup 20 has a hard edge that rests against a wearer's body and, even with the padding 24 and the thickness of the pouch 14, can dig into the user's body after receiving a localized bow. In addition, the cup's edge can chafe against the wearer's skin during the athletic activity. It has proven difficult to eliminate chafing using a rigid cup because the rigidity that makes the cup 20 effective protection against localized blows also causes the cup 20 to be unyielding against the body of an athlete who is performing extreme leg, hip and pelvic movements typical during athletic activity. In addition, the foam padding 24 itself is relatively thin and semi-rigid, especially about the rim of the cup 20, and can not compensate for the rigidity of the cup 20. It does not have enough "give" to accommodate the wide range of movements made by an athlete.

A number of improvements to cup design have been suggested. U.S. Pat. No. 1,830,572, to Taylor, describes an athletic supporter having a rigid, unyielding cup with an inner rim of sponge rubber and rests on additional pads to assist in distributing the rearward force of blows. The cup is cemented to an outwardly facing chamber filled with gas under pressure to distribute forces over the entire surface area of the cup. Such padding ameliorates the above-described discomforts to a certain extent, but chafing is not eliminated and the cup's edge can still be felt after receiving a hard blow. Therefore, such devices reduce the probability of injury to a certain extent, but, being rigid, the cups can not provide protection against chafing during extreme athletic activity.

Gel materials have been used in the past in athletic devices to protect against the chafing brought on by constant or near constant contact against hard surfaces. For example, U.S. Pat. No. 5,103,505 discloses the use of gel filled pads in the seat portion of a pair of boxer shorts to act as a seat cushion for invalids or audience members at sporting events. In addition, gel pads have been used in sports equipment (such as in bicycle gloves, bicycle seats, running shoes, and ice skates). While these provide some protection against chafing from constant and near constant contacts, typically they have been incorporated into applications involving a limited range of body movements. In addition, they have not been incorporated into applications requiring protection from localized blows having great force.

SUMMARY OF THE INVENTION

In accordance with the present invention, there is provided a cushioning pad sized to be disposed about the inguinal area of a human male and to be worn for the support and protection of said area. The cushioning pad contains a gel material to protect against both localized blows and chafing. The pad fits into a protective garment comprising a waist band and a pouch depending from the waist band and having a pocket sized to receive the pad. The pouch further has a top portion attached to the waist band and a bottom portion. The garment further has a securing means for securing the pouch about the inguinal area by connecting the bottom portion of the pouch to the waist band. Preferably, the securing means is a pair of leg straps that connects the bottom portion of the pouch to the waist band.

In one embodiment, the pad further comprises an inner layer of gel material, an outer layer of gel material, and a layer of shaping material disposed therebetween. In one aspect of the invention, the layer of shaping material comprises a rigid layer of shaping material such as a heavy plastic. In the preferred embodiment, the layer of shaping material is a flexible, non-rigid material such as a thin layer of plastic.

The inner layer and outer layer of gel material may both have approximately the same thickness of ¼ inch so that the pad is approximately ½ inches thick. Preferably, the layer of shaping material may be sized to be shorter and narrower than the inner layer and outer layer of gel material so that the layer of shaping material is completely interior to the cushioning pad, and no sharp or blunt plastic edges can come into contact with the body of the athlete. In one embodiment, the inner layer and outer layer have approximately the same width and length, with the width and length of the layer of shaping material being approximately 1 inch shorter than the width and length of the inner and outer layers so that the outer rims of the inner and outer layers are in contact with each other.

The pad may be curved with an outer side that is convex and an inner side that is concave. In one embodiment, the shaping results from the layer of shaping material having an outer surface that is generally convex and an inner surface that is generally concave. In another embodiment, the layer of shaping material has a bottom portion and a top portion, and at least one of the portions is shaped with a convex outer surface in contact with the outer layer of gel material and a concave inner surface in contact with the inner layer of gel material.

The gel material may comprise silicon gel or the gel marketed under the trademark Memoflex by Trico Sports of Pacoima, Calif. In addition, the pad may have a cover of woven material holding the gel material.

In accordance with a further aspect of the invention, there is disclosed a protective garment to be worn for the support and protection of the inguinal area of a human male. The garment comprises a waist band, a pouch disposed about the inguinal area when the garment is worn, and, disposed within the pouch, a cushioning pad containing a gel material. The pouch has a top portion attached to the waist band, a bottom portion, and a pocket to receive the pad. The garment also has securing means to secure the pouch about the inguinal area. Preferably, the securing means is a pair of leg straps that connects the bottom portion of the pouch to the waist band.

In accordance with yet another aspect of this invention, a method for supporting and protecting the inguinal area of a human male comprises wearing about the inguinal area a cushioning pad containing a gel material.

In accordance with yet another aspect of this invention, a method is disclosed for forming a cushioning pad. The method comprises providing an inner layer of gel material, and placing, above the inner layer, a layer of shaping material that covers essentially all of the inner layer except its outer edge. Additionally, an outer layer of gel material that extends at least to the outer edge of the inner layer can be provided. The inner and outer layers can be formed by pouring them into a mold. The pad may be formed by pouring into a mold an inner layer of gel material that extends at least around an outer rim of the mold; when the gel material is partially set, fitting, above the inner layer, a layer of shaping material having an outer edge; and pressing the layer of shaping material into the inner layer so that the gel material oozes up and over the outer edge of the layer of shaping material to form an outer layer of gel material. In yet another embodiment, the pad is formed by forming a first and second sheets of gel material to operate as an inner layer and an other layer respectively; and attaching therebetween a layer of shaping material.

BRIEF DESCRIPTION OF THE DRAWINGS

The above-mentioned and other features of the invention will become more apparent by reference to the following description taken in connection with the accompanying drawings in which.

DESCRIPTION OF THE PREFERRED EMBODIMENTS

Figure 1:
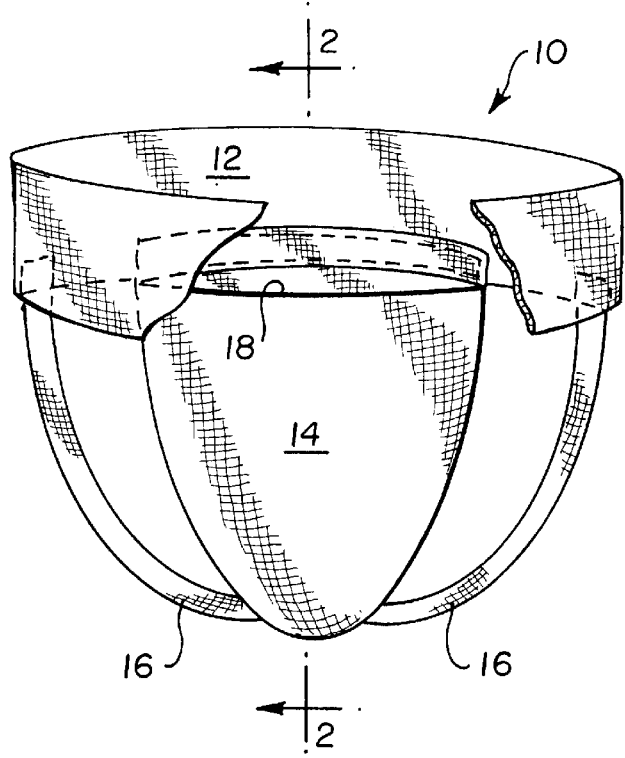
FIG. 1 is a rear perspective view of an athletic supporter.
Figure 3:
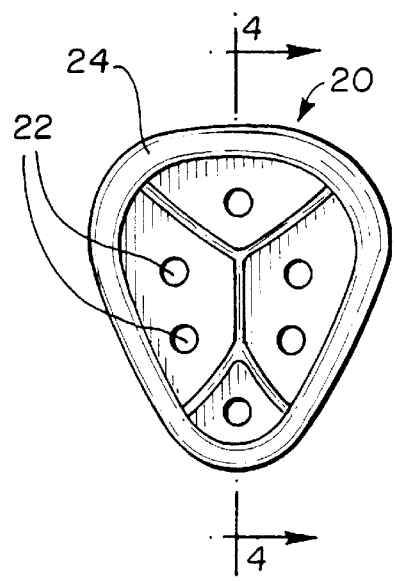
FIG. 3 is a front perspective view of a typical rigid athletic shield.
Figure 2:
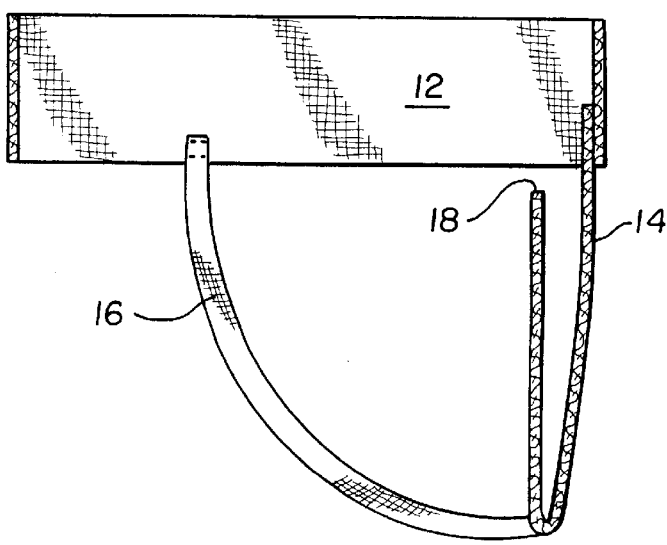
FIG. 2 is a side view taken along line 2—2 of FIG. 1.
Figure 4:
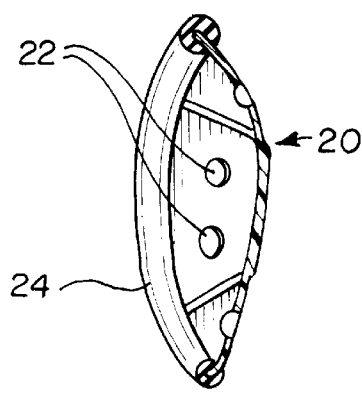
FIG. 4 is a side view taken along line 4—4 of FIG. 3.

Referring now to FIG. 1, a support garment 10, in accordance with a preferred embodiment of the invention, is shown. The garment 10 is in the form of an athletic supporter, comprising an elastic waist band 12 and a genital pouch 14 attached to the front of the waist band 12 and depending downward from the waist band 12. Two leg straps 16 are sewn to the bottom of the pouch and to opposite sides of the waist band 12 at positions removed from the top of the pouch 14. The pouch 14 is preferably made of fabric, and it may be elasticized in a conventional manner.

Figure 5:
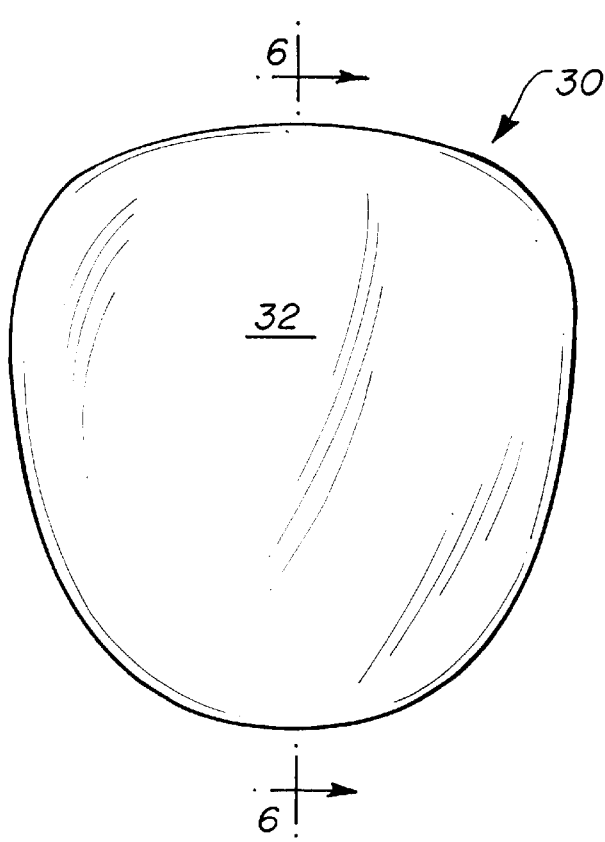
FIG. 5 is a front perspective view of a cushioning pad of the present invention to be used in conjunction with the athletic supporter of FIG. 1.
Figure 6:
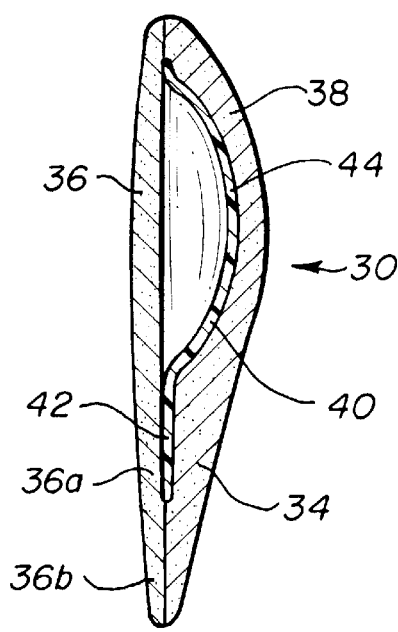
FIG. 6 is a side view taken along line 6—6 of FIG. 5.

The pouch 14 has a top-opening pocket 18. In the preferred embodiment, the pocket 18 is disposed to open to the rear of the pouch 14, toward the body of a wearer. However, the garment 10 may be arranged so that the pocket 18 is disposed to open to the front of the pouch 14. The pocket 18 is sized and configured to receive the pad 30 that is shown in FIGS. 5–6. In the preferred embodiment, the pad 30, consisting of a cover 32 holding a gel material 34, is approximately ½ inch thick. In use, the pad 30 is held in position over the inguinal area by the garment 10, protecting the inguinal areas from localized blows and chafing.

In the preferred embodiment, as best shown in FIG. 6, the pad 30 is formed of an inner layer 36 of gel material, an outer layer 38 of gel material, and a relatively thin layer 40 of shaping material disposed between the layers 36, 38, intended to assist the pad 30 in retaining its shape after being subjected to sharp blows. The layers 36, 38 may both have approximately the same thickness of ¼ inch thick. The layer 40 of shaping material is a flexible, non-rigid material such as a thin layer of plastic. In another embodiment, described below, the shaping material may be a rigid material such as a heavy plastic. Returning to the preferred embodiment, the cover 32 of the pad 30 is a washable, breathable woven material having a low coefficient of friction, such as the nylon used in bathing suit liners. The cover 32 may be removable for washing, being provided with a releasable closure such as Velcro tabs. Alternatively, the cover 32 may have fitted over it a releasable washable cover.

To better fit the pad 30 against the inguinal area of a wearer, the pad 30 may be curved with an outer side that is convex and an inner side that is concave. The approximate angles of curvatures are shown in FIG. 6. It is useful to note that the angles may be chosen to be smaller than the angles of curvature embodied in the standard rigid cup 20. The cup 20 requires large angles of curvature because it is must be sized large enough to contain without contacting the male genitalia. Otherwise, the cup 20 would contact the genitalia during sharp blows. On the other hand, the pad 30 may at least occasionally contact the genitalia, because the resiliency and blow-absorbing characteristics of the gel material will protect the genitalia. Therefore, the contours of the pad 30 can be more subtle than those of the standard cup 20.

In one embodiment, the shaping results from the layer 40 of shaping material having an outer surface that is generally convex and an inner surface that is generally concave. In another, preferred embodiment, shown in FIG. 7, the layer 40 has an essentially planar bottom portion 42 and a top portion 44 that is shaped with a convex outer surface in contact with the outer layer 38 of gel material and a concave inner surface in contact with the inner layer 36 of gel material.

Figure 7:
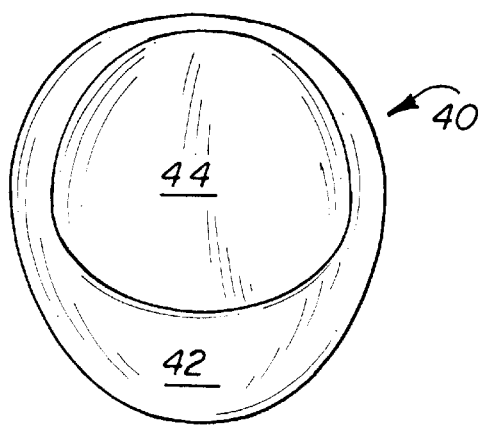
FIG. 7 is a front perspective view of the shaping member shown in FIG. 6.

Returning to FIG. 6, and comparing FIG. 7 to FIG. 5, the layer 40 of shaping material is shorter and narrower than the inner layer 36 and outer layer 38. As seen in FIG. 6, the inner layer 36 has two sections: a first section 36a disposed below the rim of the layer 40; and a second section 36b disposed beyond the first section 36a. The layers 36, 38 have approximately the same width and length, and the layer 40 is approximately 1 inch shorter in length and narrower in width, so that, when the pad 30 is assembled, the outer rims of the layers 36, 38 are in contact with each other. The second section 36b is sized so that the layer 40 does not extend over the second section 36b, thus preventing contact between the rim of layer 40 and the skin of a wearer of the pad. The layer 40 is completely interior to the cushioning pad 30. In this way, no sharp or blunt plastic edges contact the body of the athlete. Therefore, the only contact made by the device is the gel material, further padded by the pouch 14. Chafing is thus minimized.

The gel material may comprise silicon gel or, preferably, a gel sold in sheets under the trademark "Memoflex" by Trico Sports of Pacoima, Calif. The pad 30 is manufactured from sized and cut sheets of gel and shaping materials. They may be joined by the holding action of the cover 32 or glued or otherwise affixed together. Preferably, the pad 30 may be formed by molding a liquid form of gel material, and allowing it to cure: first pouring the liquid into a mold to form the inner layer 36, then fitting above it the layer 40 of shaping material, pouring the liquid gel material above the layer 40 to form the outer layer 38, and allowing the gel material to set. Alternatively, the pad 30 may be molded by suspending the layer 40 of shaping material within a mold, then pouring the liquid gel material around the layer 40 to form layers 36, 38, then allowing the material to set.

Figure 8:
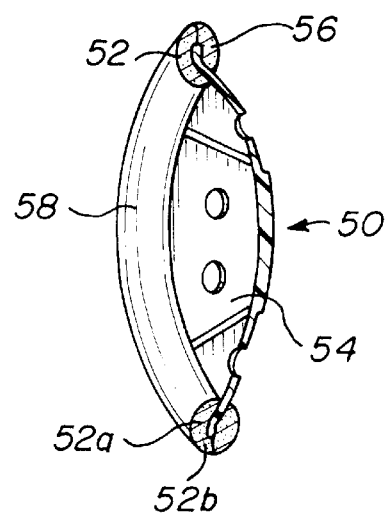
FIG. 8 is a side cut-away view of another embodiment of the invention.

In another embodiment, as shown in FIG. 8, a cushioning pad 50 comprises an inner layer 52 of gel material, an outer layer of gel material 56, and a rigid layer of shaping material such as a heavy plastic, shaped as a conventional cup 54. The inner layer 52, which may or may not extend along the entire interior surface of the cup 54, has two sections: a first section 52a disposed below the rim of the cup 54; and a second section 52b disposed along and beyond the first section 52a. The second section 52b, extends along and beyond the rim of the cup 54 by about ½ inch. The second section 52a is sized so that the cup 54 does not extend over the second section 52b, thus preventing contact between the rim of the cup 54 and the skin of a wearer of the pad. The outer layer 56, which preferably does not extend along the entire surface of the cup 54, extends along and beyond the rim of the cup 54 also by about ½ inch, so that the rim of the cup 54 is completely interior to the cushioning pad 50. In this way, no sharp or blunt plastic edges contact the body of the athlete.

Preferably, the pad 50 has a cover 58 made from a washable, breathable stretchy material having a low coefficient of friction. The pad 50 is manufactured by molding: first pouring the inner layer 52, then fitting above it the cup 54, then pouring the outer layer 56. Alternatively, the pad 50 is formed by first pouring the inner layer 52; then, when the inner layer 52 is partially set, fitting above it the cup 54; and finally pressing the cup 54 down into the layer 52 so that the layer 52 oozes up and over the outer rim of the cup 54, thereby forming the outer layer 56.

It should be appreciated that the dimensions of the supporter 10 and the pads 30, 50, including the elements thereof and the angles of convexity and concavity, can be changed without altering the spirit of the invention.

Having described preferred embodiments of the invention, it will now become apparent to those of skill in the art that other embodiments incorporating its concepts may be provided. It is felt therefore that this invention should not be limited to the disclosed embodiments but rather should be limited only by the spirit and scope of the appended claims.

What is claimed is:

1. A protective device for cushioning, supporting and protecting the inguinal area of a human male, said protective device comprising:

a pad for cushioning, supporting and protecting the inguinal area of a human male, said cushioning pad having
  a layer of shaping material having sufficient volume to enclose the male genitals and sized to be disposed about the inguinal area of a human male, said layer of shaping material having a rim about the circumference thereof, and
  an inner layer containing a gel material and having a first section disposed below said rim of said layer of shaping material, said first section adapted to contact the body proximate to the inguinal area and to absorb blows experienced by said pad, said first section providing cushioning between said rim of said layer and the skin of a wearer of said pad; and
 means for holding said pad in position over said inguinal area,
wherein chafing and blows to said inguinal area are absorbed by said gel material.

2. The cushioning pad of claim 1, wherein said means for holding is a protective garment comprising a waist band; a pouch depending from said waist band and having a top portion attached to said waist band, a pocket sized to receive said pad, and a bottom portion; and securing means for connecting said bottom portion to said waist band for securing said pouch about said inguinal area.

3. A protective garment comprising
 a pad for cushioning, supporting and protecting the inguinal area of a human male,
 a waist band;
 a pouch depending from said waist band and having a top portion attached to said waist band, a pocket sized to receive said pad, and a bottom portion; and
 securing means for connecting said bottom portion to said waist band for securing said pouch about said inguinal area,
said cushioning pad further comprising
  a layer of shaping material having sufficient volume to enclose the male genitals and sized to be disposed about the inguinal area of a human male, said layer of shaping material having a rim about the circumference thereof, and
  an inner layer containing a gel material and having a first section disposed below said rim of said layer of shaping material, said first section adapted to contact the body proximate to the inguinal area and to absorb blows experienced by said pad, said first section providing cushioning between said rim of said layer and the skin of a wearer of said pad,
wherein chafing and blows to said inguinal area are absorbed by said gel material.

4. The protective device of claim 3, wherein said gel material comprises silicon gel.

5. The protective device of claim 3, wherein said pad further comprises a fabric cover holding said gel material.

6. The protective device of claim 3, wherein said pad is curved with an outer side that is convex and an inner side that is concave.

7. The protective device of claim 3, wherein said layer of shaping material has a width and length less than the width and length of said inner layer, and said inner layer has a second section disposed beyond said first section and sized so that said layer of shaping material does not extend over said second section, said second section preventing contact between said rim of said layer and the skin of a wearer of said pad.

8. The cushioning pad of claim 7, wherein at least part of said layer of shaping material has an outer surface that is generally convex and an inner surface that is generally concave.

9. The protective device of claim 7, wherein said layer of shaping material is flexible and non-rigid.

10. The protective garment of claim 7, wherein said pad further comprises an outer layer of gel material, with said inner layer and said outer layer being approximately the same width and length so that said layer of shaping material is interior to said inner layer and said outer layer.

11. The protective garment of claim 10, wherein said outer layer is approximately ¼ inch thick.

12. The protective garment of claim 10, wherein said inner layer has approximately the same thickness as said outer layer.

13. The protective garment of claim 7, wherein said pad further comprises an outer layer of gel material, with said inner layer, said outer layer, and said layer of shaping material all having outer edges, and said outer edge of said inner layer is in contact with said outer edge of said outer layer, with said outer edge of said layer of shaping material completely interior to said inner layer and said outer layer.

14. The protective garment of claim 7, wherein said inner layer is approximately ¼ inch thick.

15. The protective garment of claim 7, wherein said layer of shaping material has a bottom section and a top section, at least one of said sections shaped with a convex outer surface in contact with said outer layer and a concave inner surface in contact with said inner layer.

16. The cushioning pad of claim 3, wherein said layer of shaping material is rigid.

* * * * *